(12) United States Patent
Hu

(10) Patent No.: US 10,743,797 B2
(45) Date of Patent: Aug. 18, 2020

(54) FIBER-OPTIC SENSORS AND METHODS FOR MONITORING MICRO-MOVEMENTS

(71) Applicant: SHENZHEN DARMA TECHNOLOGY CO., LTD., Shenzhen, Guangdong Province (CN)

(72) Inventor: Junhao Hu, Shenzhen (CN)

(73) Assignee: SHENZHEN DARMA TECHNOLOGY CO. LTD., Shenzhen, Guangdong Province (CN)

( * ) Notice: Subject to any disclaimer, the term of this patent is extended or adjusted under 35 U.S.C. 154(b) by 293 days.

(21) Appl. No.: 15/578,651

(22) PCT Filed: Aug. 26, 2016

(86) PCT No.: PCT/US2016/048928
§ 371 (c)(1),
(2) Date: Nov. 30, 2017

(87) PCT Pub. No.: WO2017/035452
PCT Pub. Date: Mar. 2, 2017

(65) Prior Publication Data
US 2018/0160947 A1    Jun. 14, 2018

Related U.S. Application Data

(60) Provisional application No. 62/210,901, filed on Aug. 27, 2015.

(51) Int. Cl.
*A61B 5/11* (2006.01)
*A61B 5/113* (2006.01)
(Continued)

(52) U.S. Cl.
CPC .......... *A61B 5/1126* (2013.01); *A61B 5/0205* (2013.01); *A61B 5/1036* (2013.01);
(Continued)

(58) Field of Classification Search
CPC .... A61B 2562/0233; A61B 2562/0266; A61B 5/1102; A61B 5/11; A61B 5/1126; A61B 5/0205
See application file for complete search history.

(56) References Cited

U.S. PATENT DOCUMENTS

| 4,931,771 A | 6/1990 | Kahn |
| 5,134,281 A | 7/1992 | Bryenton et al. |

(Continued)

FOREIGN PATENT DOCUMENTS

| JP | 2012065911 | * | 4/2012 |
| WO | 96/08197 A1 | | 3/1996 |

OTHER PUBLICATIONS

JP2012065911 machine google tranlation Nov. 2019.*
(Continued)

*Primary Examiner* — George R Evanisko
(74) *Attorney, Agent, or Firm* — Cheng-Ju Chiang

(57) ABSTRACT

A sensor for detecting micro-movements is provided herein. In various embodiments, the sensor includes a looped structure formed of a continuous multi-mode optical fiber arranged into a plurality of loops disposed substantially in a plane. Each loop within the looped structure is partially overlapping yet laterally offset from neighboring loops. The sensor further includes a light source coupled to a first end of the looped structure, a receiver coupled to a second end of the looped structure, and one or more control and processing modules. Related methods of manufacture and use are also disclosed.

18 Claims, 11 Drawing Sheets

(51) Int. Cl.
*A61B 5/0205* (2006.01)
*A61B 5/103* (2006.01)
*G01D 5/353* (2006.01)
*A61B 5/024* (2006.01)

(52) U.S. Cl.
CPC .............. *A61B 5/11* (2013.01); *A61B 5/1102* (2013.01); *A61B 5/113* (2013.01); *A61B 5/1116* (2013.01); *G01D 5/35374* (2013.01); *A61B 5/02444* (2013.01); *A61B 2562/0233* (2013.01); *A61B 2562/0266* (2013.01)

(56) References Cited

U.S. PATENT DOCUMENTS

| | | | |
|---|---|---|---|
| 5,256,237 A | 10/1993 | Maas et al. | |
| 5,649,035 A * | 7/1997 | Zimmerman | G01B 11/18 250/227.14 |
| 5,900,556 A | 5/1999 | Ahmad et al. | |
| 6,498,652 B1 | 12/2002 | Varshneya et al. | |
| 7,702,189 B2 | 4/2010 | Sanders | |
| 2012/0203117 A1 | 8/2012 | Chen et al. | |
| 2015/0185014 A1* | 7/2015 | Yoshida | G01C 19/722 356/460 |
| 2016/0089059 A1 | 3/2016 | Hu | |
| 2018/0242900 A1* | 8/2018 | Kuwa | A61B 5/11 |

OTHER PUBLICATIONS

Augustin Grillet, Damien Kinet, Jens Witt, Marcus Schukar, Katerinea Krebber, Fabrice Pirotte, Annick Depre, "Optical Fiber Sensors Embedded into Medical Textiles for Healthcare Monitoring", IEEE Sensors Journal, Jul. 2008, pp. 1215-1222, vol. 8 Issue 7, IEEE.

* cited by examiner

FIBER-OPTIC SENSORS AND METHODS FOR MONITORING MICRO-MOVEMENTS

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of fiber optics, and more specifically, to improved optical fiber sensor configurations and related methods of manufacture and use.

BACKGROUND

With the advent of internet-connected devices and the digital health industry, health and wellness monitoring has become an area of growing focus. Monitoring vital signs such as heart rate, ballistocardiogram signals, and breathing rate is desirable both inside and outside healthcare facilities. Within healthcare settings, vital sign tracking can be essential for: ensuring patient safety when a healthcare provider is not present at a bedside, diagnosing medical conditions, monitoring a patient's progress, and planning a patient's care. Outside of healthcare settings, tracking vital signs and posture enables individuals to quantify and conceptualize their health status, thereby helping individuals remain mindful of their health and wellness needs, visualize progress, and maintain the motivation needed to achieve health and fitness goals.

Current vital sign trackers in the consumer market are fairly intrusive, for example, current heart rate monitors often require an individual to strap the monitor around the individual's chest. Many vital sign trackers include just one type of sensor configured to detect one type of vital sign, such as, for example, heart rate. Additionally, many vital sign monitors in the consumer market are not very accurate. In the healthcare setting, much more accurate devices are available, but they are often very large devices positionable at a patient's bedside, requiring a connection to an electrical outlet and leads attached to the patient. Attachment to these bedside devices can cause anxiety in patients, and the devices are expensive, not portable, and prone to electromagnetic interference (EMI).

Optical fiber sensors have gained increased attention in the research setting as an alternative to existing vital sign monitors. Optical fiber sensors are chemically inert and resistant to EMI. Moreover, they can be portable and integrated into fixtures, such as mattress pads and cushions. Fixture-integrated devices have numerous advantages over bedside appliances and wearable instruments. For example, fixture-integrated devices allow for a reduction in loose connecting wires or wireless data transmitters between sensors, electronics, and power supplies. This reduction may lead to increased reliability, data quality, and security.

However, optical fiber sensors developed to date have not proven to be suitable alternatives to conventional monitoring systems. For example, in "Optical Fibre Sensors Embedded into Medical Textiles for Healthcare Monitoring," *IEEE Sensor J.* 8 (7), 1215-1222, 2008, Grillet et al. proposed integrating a single mode macro-bending fiber sensor into a belt to measure respiratory rate. A macro-bending sensor typically experiences significant light loss due to macroscopic deviations in the fiber's axis from a straight line, resulting in low sensitivity. Such a sensor would be unlikely to detect the subtle movements of the chest wall needed to accurately measure heart rate or ballistocardiogram signals.

In an effort to improve sensitivity, others have proposed alternative approaches for fiber optic sensors. For example, in U.S. Pat. No. 6,498,652, Varshneya et al. disclosed a fiber optic monitor that utilizes optical phase interferometry to monitor a patient's vital signs. Optical phase interferometry has several limitations, for example, it requires an expensive phase modulator and coherent optical sources, which adds significant cost and complexity and makes it impractical for widespread commercial adoption. Other proposed designs have struggled to balance sensitivity, accuracy, and cost. Thus, there is a need for new and useful optical fiber sensors.

SUMMARY

The present disclosure provides new and useful optical fiber sensors and related systems and methods for posture and vital sign monitoring. Various embodiments provided herein overcome one or more of the shortcomings of previously designed fiber optic vital sign monitoring systems.

One aspect of the disclosure is directed to a sensor for detecting micro-movements, for example, physiological micro-movements. In various embodiments, the sensor includes a looped structure formed of a continuous multi-mode optical fiber arranged into a plurality of loops disposed substantially in a plane. Some of or all loops are equal in size. Each loop within the looped structure is partially overlapping yet laterally offset from neighboring loops. The sensor further includes a light source coupled to a first end of the looped structure and a receiver coupled to a second end of the looped structure. The receiver is configured to sense changes in an intensity of light traveling through the looped structure. The sensor of some embodiments further includes a driver driving the light source and one or more structures to process the light received at the receiver. For example, in some embodiments, the sensor includes a signal amplifier and an analog-to-digital (AD) converter. In some embodiments, the sensor includes a signal filter. In various embodiments, the sensor also includes a control and processing module.

In some embodiments, the sensor is a pressure sensor, force sensor, or vibration sensor. In some embodiments, the continuous multi-mode optical fiber has a core diameter that is greater than 49% of the total diameter of the continuous multi-mode optical fiber.

In some embodiments, each of the loops forms a square, other rectangle, or other parallelogram. In other embodiments, each of the loops forms a circle or other ellipse. Alternatively, in still other embodiments, each of the loops forms a matching irregular shape.

In some embodiments, the continuous multi-mode optical fiber is formed of glass, plastic, or other suitable material.

In some embodiments, the sensor comprises a plurality of looped structures. In some such embodiments, the plurality of looped structures is formed of a single continuous multi-mode optical fiber such that each of the looped structures is directly connected to the other looped structures in the sensor. In other embodiments, the plurality of looped structures includes a plurality of multi-mode optical fibers, each of the multi-mode optical fibers forming a separate looped structure. The plurality of looped structures may be positioned adjacent to each other on a plane. Alternatively, in other embodiments, the plurality of looped structures may partially or fully overlay each other.

In various embodiments, the sensor is disposed within a mattress, cushion, or other fixture or structure. In some such embodiments, the sensor is positioned below a top cover, and additionally or alternatively, in some embodiments, the sensor is positioned above a bottom cover. In some embodiments, the sensor further includes a mesh structure. In some such embodiments, the mesh structure is a single layer of mesh disposed above or below the optical fiber looped structure. In other embodiments, the mesh structure is formed of two layers of mesh which sandwich the optical fiber looped structure therebetween.

Another aspect of the disclosure is directed to a method of manufacturing a sensor for detecting micro-movements, such as, for example, any embodiment of the sensor described above or elsewhere herein. In various embodiments, the method includes: providing an axle, rotating the axle, wrapping a continuous multi-mode optical fiber around the rotating axle, and displacing the multi-mode optical fiber from the axle onto a flat plane.

In some embodiments, the axle has a plurality of coupling elements coupled thereto, which rotate with rotation of the axle. In some such embodiments, the multi-mode optical fiber becomes engaged with the coupling elements on the axle while the continuous multi-mode optical fiber is wrapped around the rotating axle. In some embodiments, displacing the multi-mode optical fiber from the axle involves disengaging the plurality of coupling elements from the axle. In other embodiments, displacing the multi-mode optical fiber from the axle involves disengaging the multi-mode optical fiber from the coupling elements. In some embodiments, the plurality of coupling elements are equally or substantially equally spaced laterally on the axle. In some embodiments, the plurality of coupling elements include one or more of tape, glue, resin, other adhesive compound, hooks, latches, or other physical coupling elements.

In still other embodiments, the axle includes a groove or other surface feature running along a length of the axle surface in an axial direction, and a wedge, rod, or other tool can be inserted into or removed from the groove, under the wound multi-mode optical fiber to facilitate removal of the fiber from the axle.

In some embodiments, the multi-mode optical fiber is wrapped around the axle by moving an arm axially with respect to the axle from a first position to a second position parallel to the axle as the axle rotates. In such embodiments, the arm is configured to dispense the multi-mode optical fiber on the axle.

Still another aspect of the disclosure is directed to a method of detecting patient health and/or activity information. The method of various embodiments includes positioning a sensor for detecting micro-movements under a patient, such as, for example, any embodiment of the sensor described above or elsewhere herein. In various embodiments, the method further includes detecting, by the receiver, a change in an intensity of light traveling through the looped structure, and determining a patient vital from the change in light intensity. In various embodiments, the change in light intensity corresponds to fiber deformation caused by one or more micro-movements of the human body. In some embodiments, the patient health and/or activity information includes one or more of: a ballistocardiogram waveform, a heartbeat, breathing, other vital sign, body weight, posture, or a shift in body weight or posture.

DETAILED DESCRIPTION

The provided figures and the following description of certain embodiments of the invention is not intended to limit the invention to these embodiments, but rather, is provided to enable any person skilled in the art to make and use this invention. Disclosed herein are new optical fiber sensors and related methods for manufacturing and using the optical fiber sensors. Embodiments utilizing the optical fiber sensors for posture and vital sign monitoring are additionally disclosed.

Introduction

Figure 1:
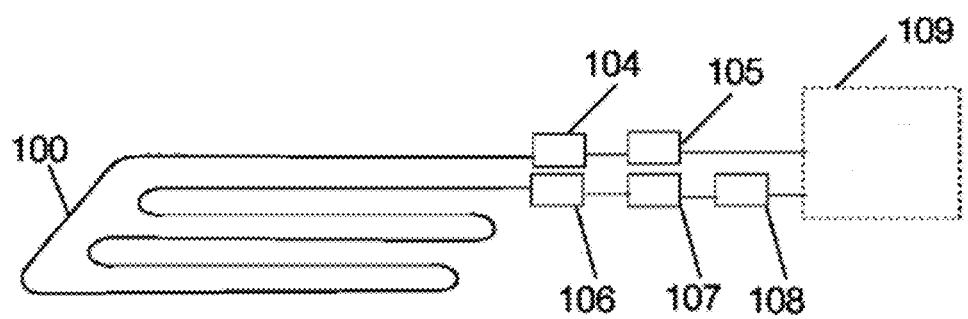
FIG. 1 illustrates a schematic diagram of one embodiment of a prior art optical fiber sensor.

Optical fiber sensor systems have previously been developed to detect applied pressure or force. As described, for example, in U.S. application Ser. No. 14/738,918 to Hu, and as shown in FIG. 1, an optical fiber sensor includes an optical fiber 100 having a first end coupled to a light source (e.g., laser, LED, OLED, etc.) 104 and a second end coupled to an optical signal receiver (e.g., a photo-detector) 106. The optical fiber may additionally be coupled to a light source driver (e.g., an LED driver) 105 at its first end and signal processing components, such as one or more of an amplifier 107, an analog-to-digital (AD) converter 108, and a filter at its second end. The light source 104 is configured to emit a light wave into the optical fiber 100. The optical fiber sensor is positioned such that an application of force on a surface causes the optical fiber 100 to deform, crimp, or microbend, which in turn influences propagation of the light wave through the optical fiber 100. Even minor deformations of the fiber 100 can result in a detectable change in light intensity within the fiber 100. The optical signal receiver 106 is configured to detect changes in light wave propagation. The changes in light wave propagation are processed and analyzed by a computing device 109 to correlate the detectable change in light intensity to environmental changes being monitored. For example, in theory, if the sensor system is sufficiently sensitive and accurate, the computing device can quantify the applied pressure, force, or change in pressure or force that caused the detected change in light wave propagation, and the applied pressure or force may be correlated to, and thus, used to detect, a position and/or vital sign of a patient.

In an effort to make optical fiber pressure or force sensors commercially viable for widespread healthcare monitoring, optical fiber sensor systems have recently been developed that utilize multimode fibers. Multimode fibers receive a plurality of modes of spectra of light from the light source, including an axial mode and at least one higher order mode. Advantageously, the equipment used in multimode fiber sensor systems is significantly less expensive and complex than the equipment needed in single mode optical fiber sensor systems.

Multi-mode fibers have a larger core diameter than single-mode fibers, with core diameters of 50 and 62.5 microns being typical. Diameters of 100 microns, 105 microns, 200 microns, or any other suitable dimensions may also be used. With multimode fibers, a transparent optical fiber forms a core that is surrounded by reflective cladding. Light entering the optical fiber at an angle will strike the cladding at an angle. If the strike angle is greater than a critical angle, the light will be reflected by the cladding back into the fiber and will continue to be guided down the length of the fiber, repeatedly bouncing off the cladding at a strike angle. If light enters at a steep angle that is less than the critical angle, then the light will pass through the cladding and be lost. Similarly, light will be lost in the fiber if there is a macro-bend in the fiber path that causes any light propagation to strike the cladding at an angle less than the critical angle. Unintended light loss, for example, from macro-bending, leads to attenuation of the signal and a decrease in sensor sensitivity and accuracy. To prevent significant light loss, each fiber has a listed bend limit, given as a minimum radius below which the fiber should not be bent.

Accordingly, as shown in FIG. 1 and in prior art publications such as US Publ. No. 2012/0203117 by Chen et al., previously proposed optical fiber sensor configurations utilize a serpentine fiber structure with bends slightly greater than the minimum radius. Typically a radius greater than 3 cm, 5 cm, or more is utilized. Such configurations strive to balance the need for relatively large bends with a desire to maximize the surface area coverage (i.e., density) of the optical fiber on a surface. Greater density corresponds to more locations of pressure or force detection on a surface. Unfortunately, as shown in FIG. 1, the relatively large bends required in the serpentine structure result in relatively large gaps between each parallel section of fiber. Thus, the surface has many locations where pressure and force cannot be detected. Accordingly, the author of this current disclosure has discovered that improved multi-mode fiber configurations are needed, which allow for increased fiber density without causing a significant increase in light loss. Such a configuration is described in detail below.

Optical Fiber Sensor System

Various embodiments of a new optical fiber sensor configuration are disclosed, which increase sensor sensitivity and sensing coverage/density of multi-mode optical fibers. The improved optical fiber sensor systems provided herein are sufficiently sensitive and accurate to detect an individual's heartbeat, ballistocardiogram signal, respiration, and/or shifts in body weight. Each of these physiological parameters or activities causes micro-movements that lead to changes in applied forces on the optical fiber when an optical fiber system having the improved optical fiber sensor configuration is positioned underneath the individual. These applied forces micro-bend the optical fiber, causing some light loss. The optical signal receiver receives the residual light propagated through the optical fiber and can identify the amount of light loss. The amount of residual light and/or light loss is processed to identify a change in applied pressure or force and thereby determine a corresponding heartbeat, respiration, and/or body movement of the patient.

Figure 2:
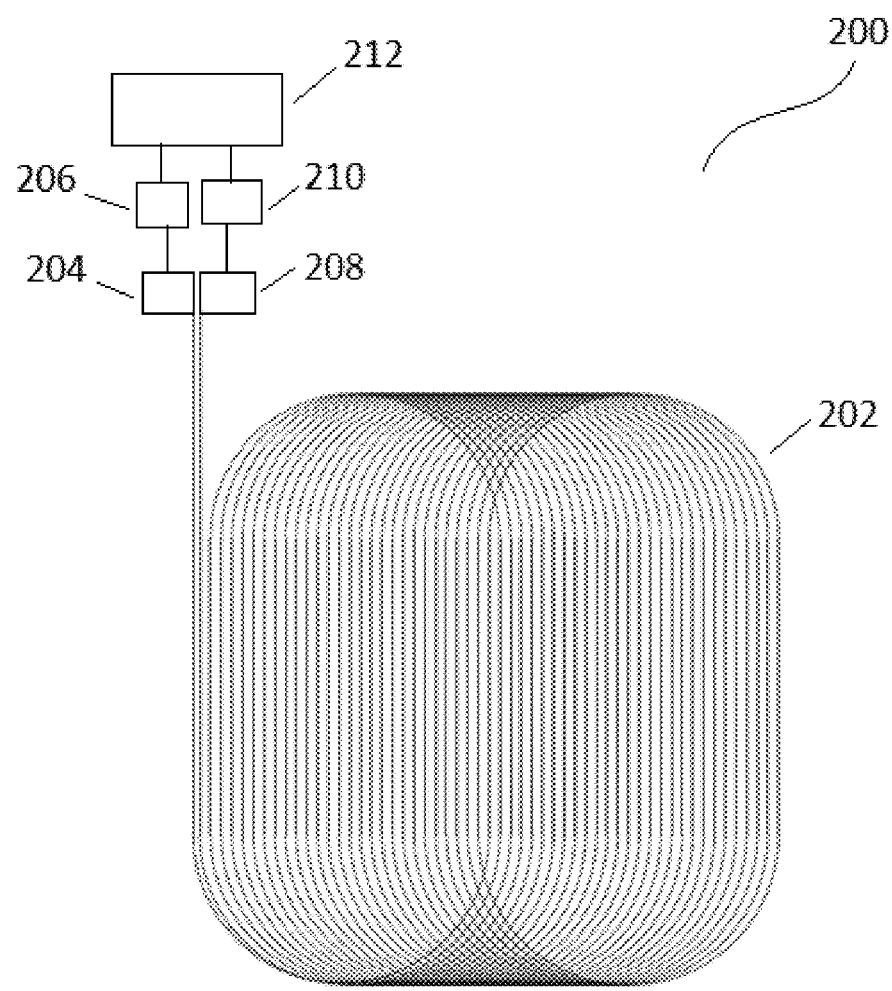
FIG. 2 illustrates a schematic diagram of one embodiment of a sensor for detecting micro-movements, in accordance with the present disclosure.
Figure 3:
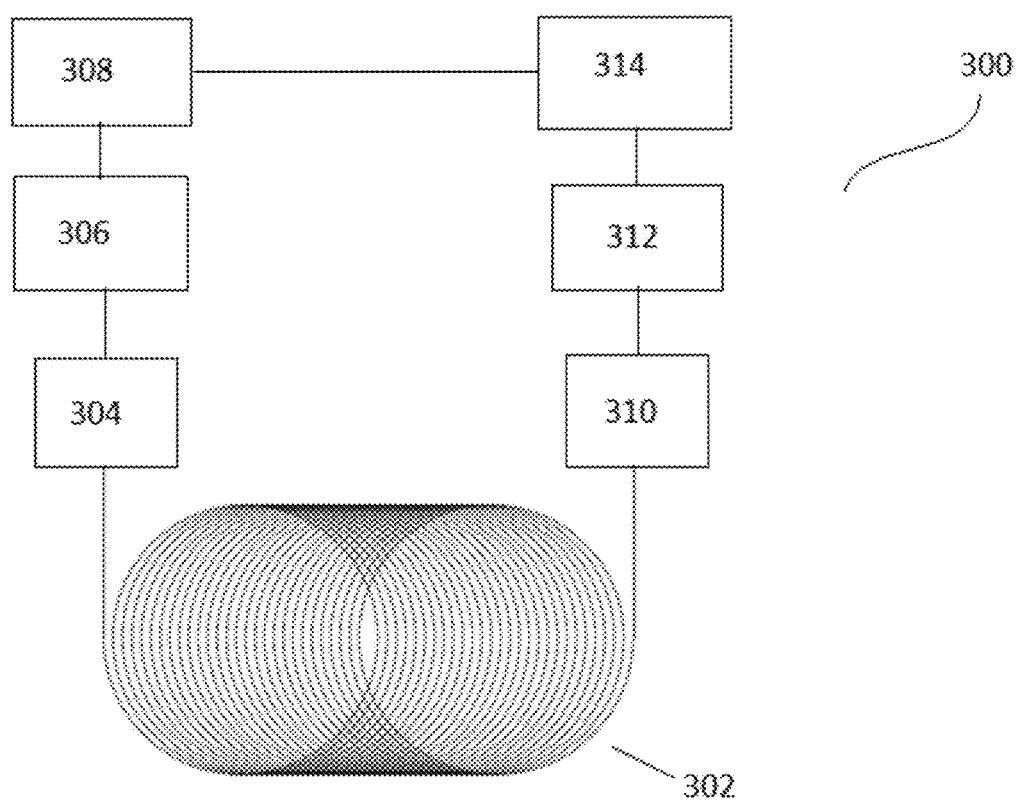
FIG. 3 illustrates a schematic diagram of another embodiment of a sensor for detecting micro-movements, in accordance with the present disclosure.

As shown in FIG. 2, the improved optical fiber sensor configuration includes one or more multi-mode fibers 202 having a looped or spiral structure. In various embodiments, the looped optical fiber structure includes a plurality of loops formed of a continuous optical fiber 202. Each loop within the looped structure is partially overlapping, yet offset from neighboring loops.

The looped structure increases the density of the optical fiber coverage compared to a serpentine configuration while also increasing the bend radius of the optical fiber 202. By minimizing tight bends in the optical fiber, the configuration decreases light loss, thereby increasing sensor sensitivity, and also decreases or slows wear on the fiber 202, reducing artifacts in the optical fiber signal caused by structurally compromised fibers. As shown throughout the drawings, in various embodiments, the looped configuration causes the optical fiber to cover significantly more of a surface than could be covered by a fiber having a serpentine configuration. For example, while a serpentine configuration typically requires at least 3 cm to 5 cm of space between each parallel fiber segment, in various embodiments provided herein, the distance between each parallel fiber segment is between 1 mm and 10 mm, and preferably, between 2 mm and 5 mm.

In some embodiments, for example, as shown in FIG. 2, each optical fiber loop 202 forms a substantially parallelogram configuration (e.g., rectangular, squared, etc.) having rounded edges. No sharp bends are present. In other embodiments, such as shown in FIGS. 3-6, the looped optical fiber structure may include a circular or elliptical configuration. In some embodiments, the looped structure may form an irregular shape having no sharp bends. The optical fiber may be formed of glass, plastic, or any other suitable material. In order to improve structural integrity and sensitivity, various embodiments of the optical fiber sensor utilize an optical fiber having a relatively large core diameter. In some embodiments, the core diameter is greater than 49% of a total diameter of the continuous multi-mode fiber. In some embodiments, the ratio of core diameter to total diameter is greater than 0.5. The total diameter includes the diameter of the core fiber and the outer cladding. In some embodiments, the core diameter forms 49-88% of the total diameter of the multi-mode fiber. In some embodiments, a fiber having a total diameter of 125 microns is used. In some such embodiments, the core fiber has a diameter of 62.5 to 110 microns, and preferably, 90-110 microns. In other embodiments, a fiber having a total diameter of 250 microns is used. In some such embodiments, the core fiber has a diameter of 180 to 220 microns. In other embodiments, any suitably sized multimode optical fiber may be used.

The looped optical fiber 202 structure of various embodiments has a first end coupled to a light source 204, such as a laser, LED, or OLED. In embodiments employing an LED, an LED driver 206 may also be provided. The LED driver functions to control current flowing through the LED. A second end of the looped optical fiber structure 202 is coupled to an optical signal receiver (e.g., a photo-detector) 208 and one or more signal processing components 210, such as, an amplifier and an AD converter. A filter, such as a band-pass filter or low-pass filter may also be provided. A control and processing module 212 also forms a portion of the optical fiber sensor 200. In some embodiments, a single control and processing module 212 is provided, which is electrically connected to both the light generation end of the fiber and the light receiving end of the fiber. In such embodiments, the control and processing module 212 may be directly coupled to the light source 204 and/or the light source driver 206 and additionally directly coupled to the signal receiver 208 and/or one or more signal processing components 210. In other embodiments, as shown, for example, in FIG. 3, a separate control module 308 and a separate processing module 314 are provided in the optical fiber sensor 300. In at least some such embodiments, the control module 308 coupled to the light generation components and the processing module 314 coupled to the light receiving components are in electrical communication with one another. In some embodiments, the light source driver and/or the signal processing components are not provided as separate components; rather, the functions of current control to the light source and/or signal processing are performed by the control and processing module(s). Additional details of the control and processing module(s) are provided further below.

Returning to FIG. 2, in some embodiments, the fiber 202 is looped in a first direction (e.g., clockwise direction) for a plurality of turns then reversed and looped in a second direction (e.g., counterclockwise turns), and the second set of loops at least partially overlap the first set of loops. Such a configuration allows the first end of the optical fiber 202 and the second end of the optical fiber 202 to run substantially parallel to each other such that all electronic components can be contained within a shared area or housing. In other embodiments, as shown, for example, in FIG. 3, the fiber 302 is looped in one direction (e.g., clockwise or counterclockwise) for the entirety of the looped structure, causing a first end of the optical fiber 302 and the second end of the optical fiber 302 to be positioned on opposing sides of the looped structure.

In some embodiments, the optical fiber sensor includes a plurality of looped structures. The sensor may include two, three, four, or more optical fiber looped structures. A sufficient number of looped structures may be provided to cover substantially all of a desired detection area. For example, if the optical fiber sensor is disposed within a seat cushion, two, three, or four looped structures may be sufficient to substantially cover the surface area of the seat cushion. If the optical fiber sensor is disposed within a mattress, eight, ten, twelve, or more looped structures may be required to substantially cover the surface area of the mattress.

Figure 4:
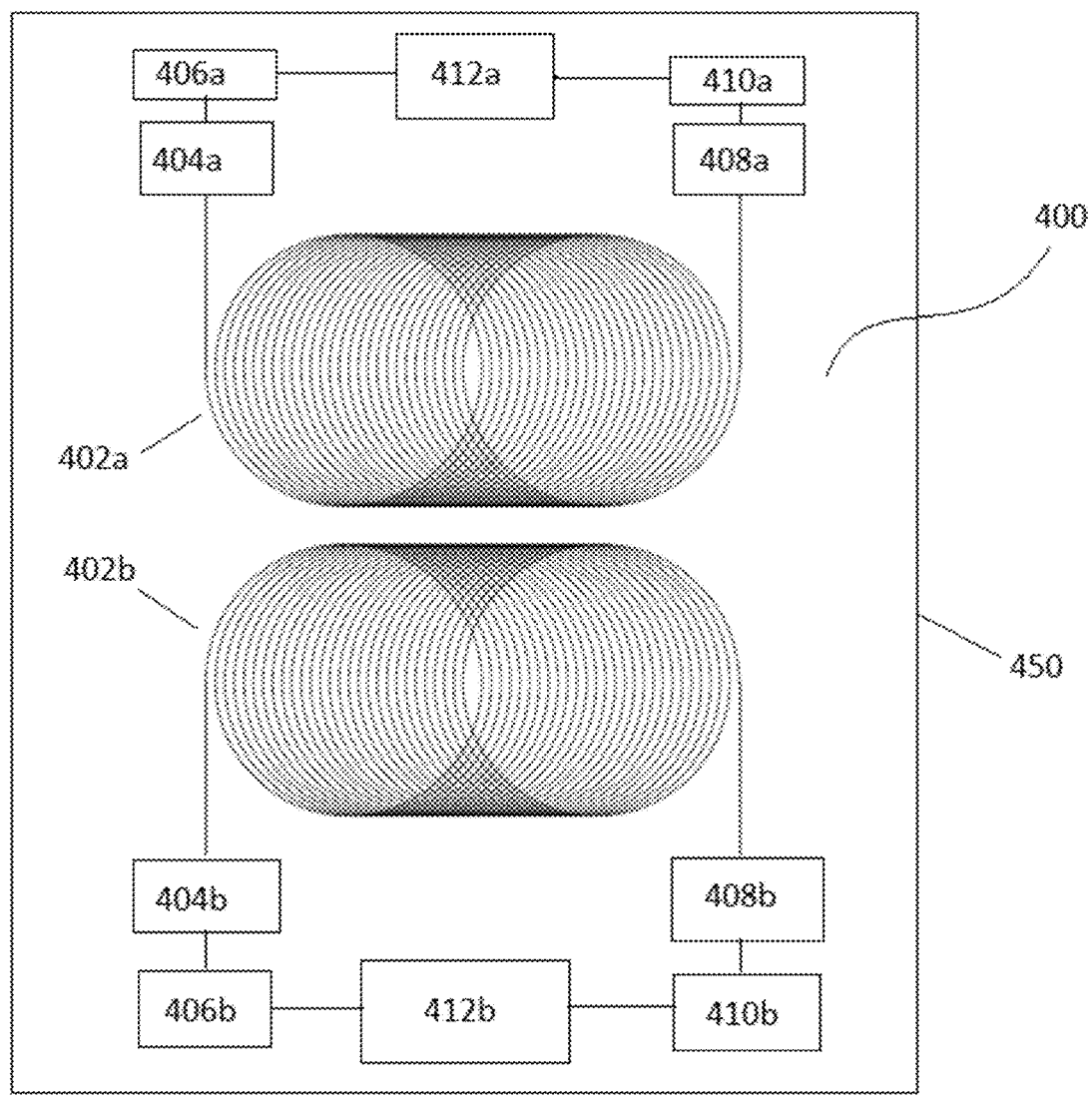
FIG. 4 illustrates a schematic diagram of another embodiment of a sensor for detecting micro-movements, in accordance with the present disclosure.
Figure 5:
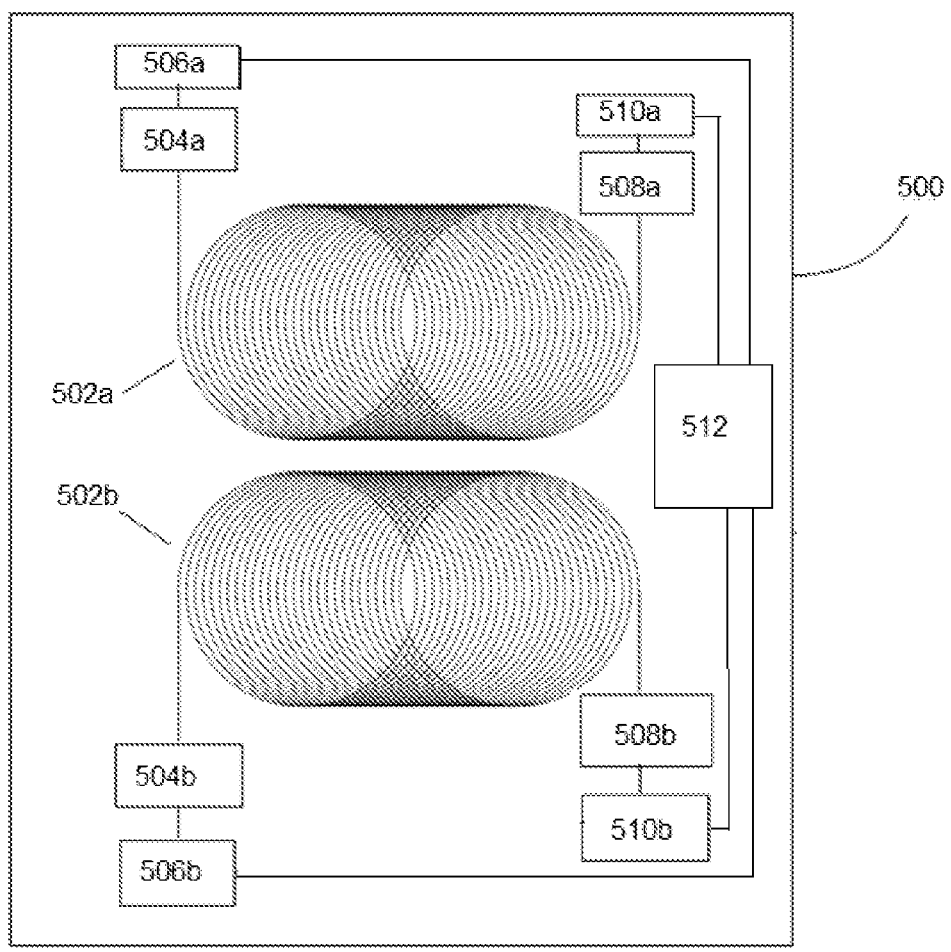
FIG. 5 illustrates a schematic diagram of another embodiment of a sensor for detecting micro-movements, in accordance with the present disclosure.

As illustrated in FIG. 4, the plurality of looped structures may each be formed of a separate, unconnected optical fiber 402a, 402b in the optical fiber sensor 400. In at least some such embodiments, each looped structure is provided with some of or all of its own set of electronic components. For example, as shown in FIG. 4, the first looped structure 402a is electrically connected to a first light source 404a, a first light source driver 406a, a first signal receiver 408a, a first set of processing components 410a, and a first control and processing module 412a. The second looped structure 402b is electrically connected to a second light source 404b, a second light source driver 406b, a second signal receiver 408b, a second set of processing components 410b, and a second control and processing module 412b. In another embodiment, as shown in FIG. 5, the first looped structure 502a is electrically connected to a first light source 504a, a first light source driver 506a, a first signal receiver 508a, and a first set of processing components 510a in yje optical fiber sensor 500. The second looped structure 502b is electrically connected to a second light source 504b, a second light source driver 506b, a second signal receiver 508b, and a second set of processing components 510b. A single control and processing module 512 is coupled to both the first looped structure 502a and the second looped structure 502b and is configured to control both light sources and process signals received via both signal receivers. In some such embodiments, all components other than the looped structures 502a, 502b are positioned on a single electronic circuit board. Such a system may save costs by using a single processor and may enable more coordinated analysis of changes in pressure distribution between the various looped structures.

Figure 6:
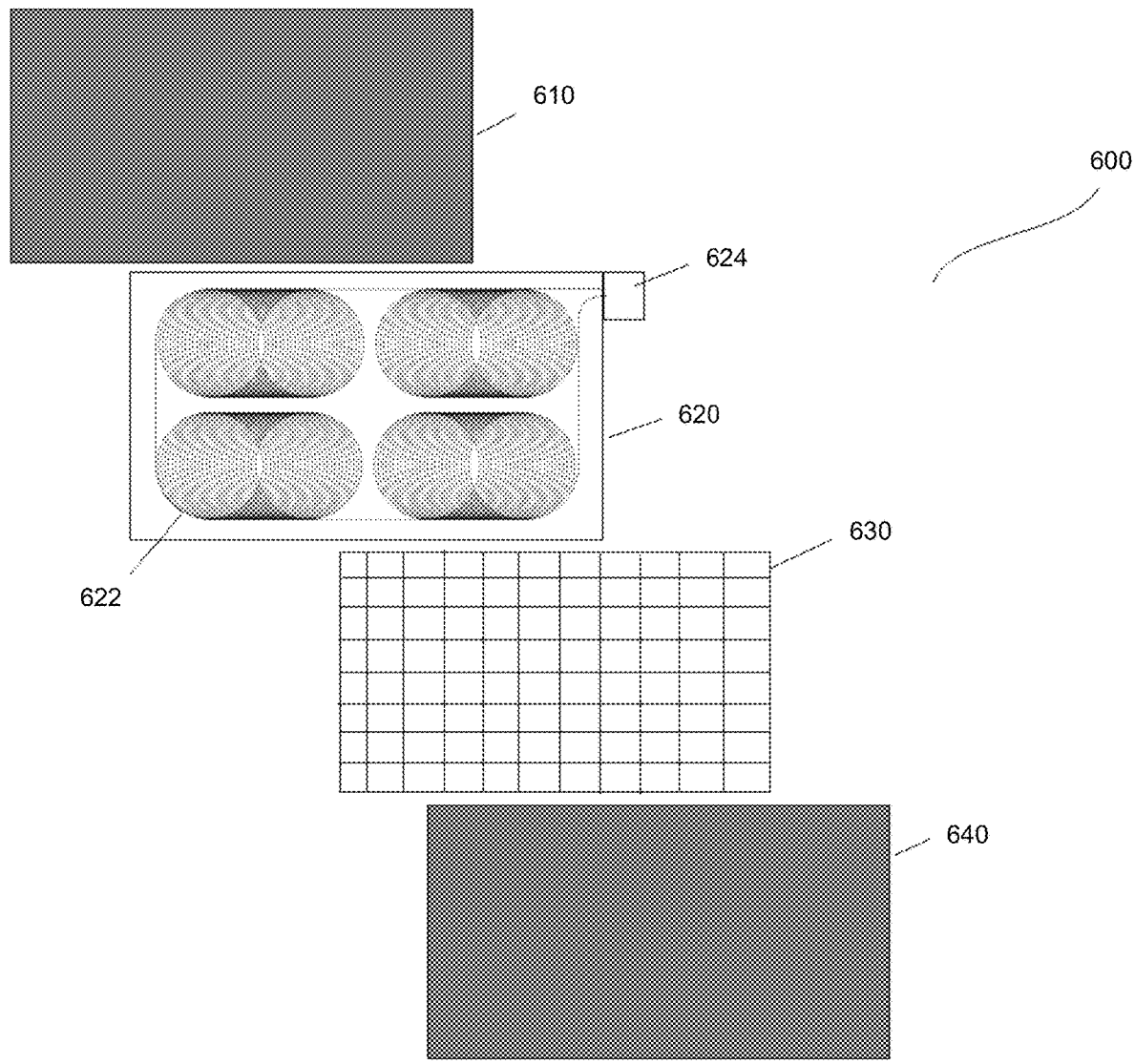
FIG. 6 illustrates an exploded schematic diagram of one embodiment of a support structure containing a sensor for detecting micro-movements, in accordance with the present disclosure.

In an alternative embodiment, such as illustrated in FIG. 6, the plurality of optical fiber looped structures may together be formed of a single optical fiber 622 such that each looped structure is connected to the other looped structures in the sensor. In such embodiments, a single set of electronic components may be provided. In the embodiment of FIG. 6, the control and processing components, the light source, and the signal receiver are all contained within a housing component 624.

Figure 7:
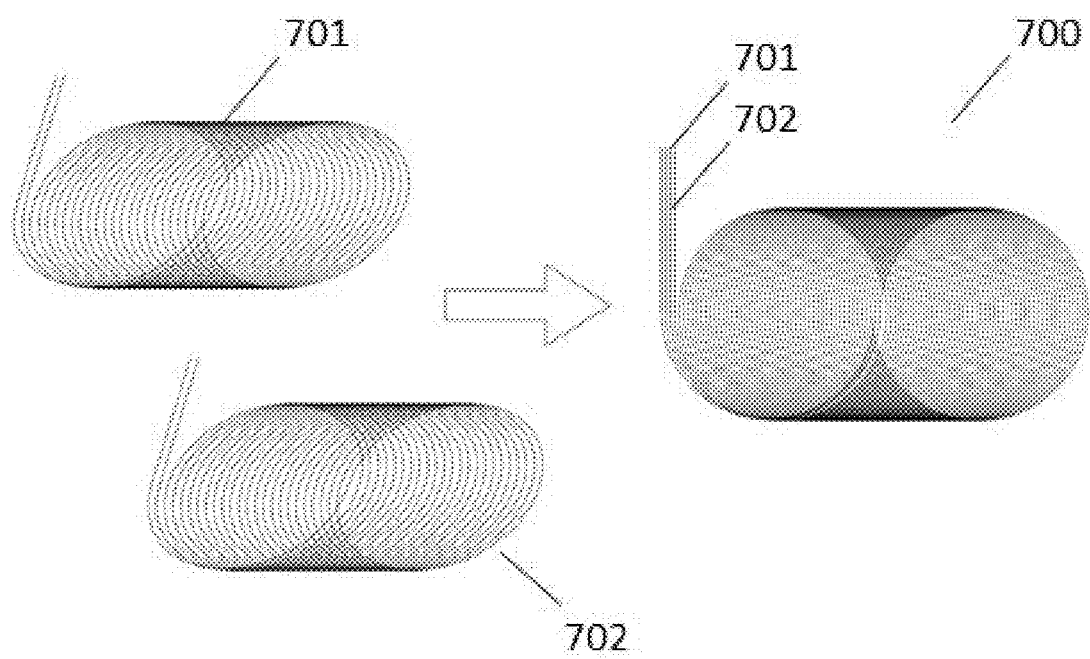
FIG. 7 illustrates a schematic diagram of one embodiment of an optical fiber configuration for placement within a sensor for detecting micro-movements, in accordance with the present disclosure.

In some embodiments, the looped structures are positioned adjacent to each other on a shared plane, as shown, for example, in FIGS. 4, 5, and 6. In other embodiments, a first looped structure 701 is configured to partially or fully overlay a second looped structure 702 to form a sensor system 700, as shown, for example, FIG. 7. In some embodiments, a plurality of two or more looped structures overlay each other.

In various embodiments of the optical fiber sensor, and as illustrated in FIG. 6, the sensing layer 620 comprising one or more looped optical fiber structures 622 is positioned between a top cover 610 and a bottom cover 640, In some embodiments, the looped optical fiber structure 622 is further sandwiched between two layers of mesh (as is typically done with the current serpentine structure). In some such embodiments, the mesh layers are formed of woven fibers, such as polyester. The mesh layers provide protection to the optical fiber. Further, the mesh layers form a mechanical structure that receives pressure exerted by a body and distributes it to the optical fiber, creating or amplifying a micro-bending effect on the optical fiber. Alternatively, in other embodiments of the sensor 600, the optical fiber looped structure 622 provides sufficient structural integrity and sensitivity that only one mesh layer 630 or no mesh layer is needed. While the sensor embodiment of FIG. 6 depicts a particular looped structure embodiment that includes four looped structures formed by a single continuous optical fiber, it is to be appreciated that any contemplated looped optical fiber structure may be positioned within the sensing layer 620.

Each of the various embodiments of the optical fiber sensor described above includes one or more control and processing module(s). The control and processing module(s) may include or consist of one or more computing devices. The control and processing module(s) may include a combination of hardware and software, which is configured to control the frequency, intensity, and/or activation of the light emitted by the light source, and which is further configured to convert the signals received from the signal receiver into meaningful data. One skilled in the art will appreciate that many different structural components and architectures may be used to achieve the functionality of the control and processing module(s). Thus, the modules will be described in functional terms.

Figure 8:
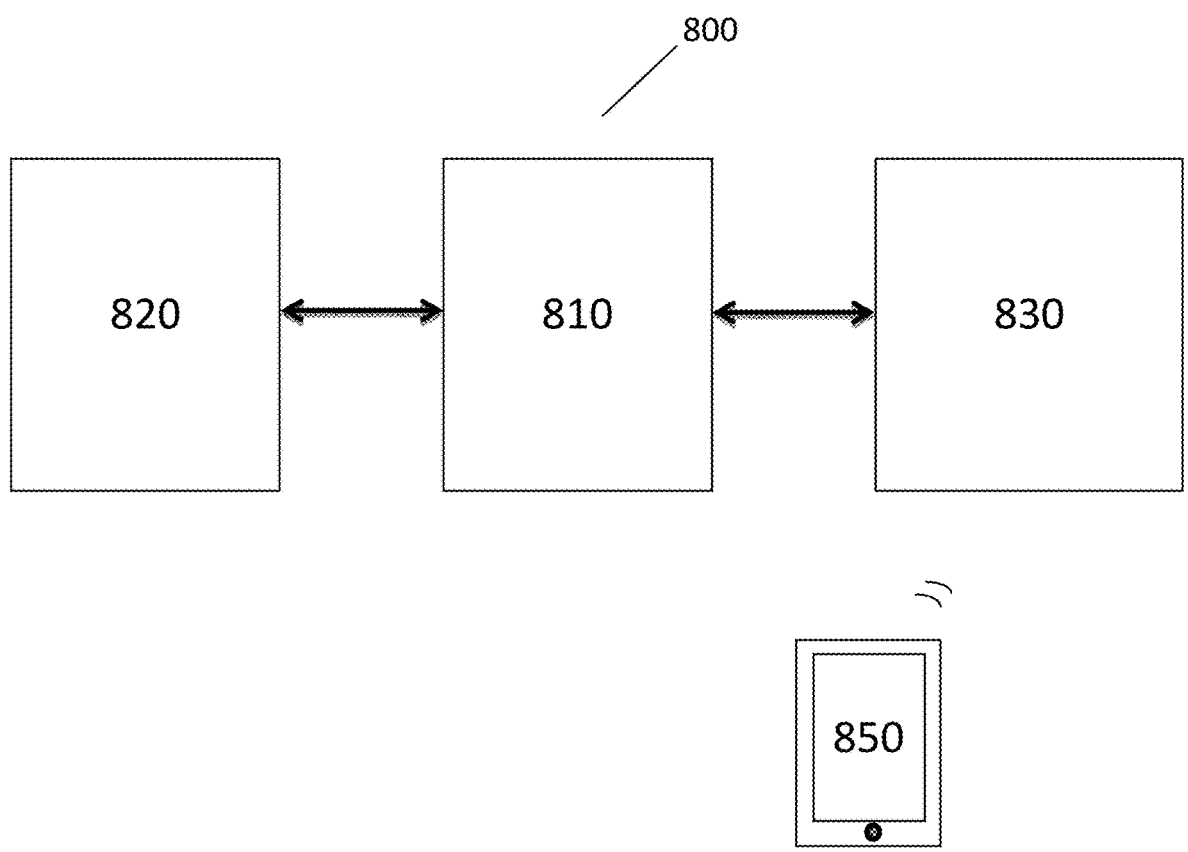
FIG. 8 illustrates a functional block diagram of one embodiment of a computing device included within an optical fiber sensor, in accordance with the present disclosure.

A functional diagram of one embodiment of a control and processing module 800 is provided in FIG. 8. Although illustrated separately, it is to be appreciated that the various functional blocks of the computing system need not be separate structural elements. For example, in various embodiments, the control and processing module 800 includes, at least, a processor 810 in data communication with memory 820 and an interface 830, and these components may be embodied in a single chip or two or more chips.

The processor 810 may be a general purpose microprocessor, a digital signal processor (DSP), a field programmable gate array (FPGA), an application specific integrated circuit (ASIC), or other programmable logic device, or other discrete computer-executable components designed to perform the functions described herein. The processor 810 may also be formed of a combination of computing devices, for example, a DSP and a microprocessor, a plurality of microprocessors, one or more microprocessors in conjunction with a DSP core, or any other suitable configuration.

In various embodiments, the processor 810 is coupled, via one or more buses, to the memory in order to read information from and write information to the memory 820. The processor 810 may additionally or alternatively contain memory 820. The memory 820 can include, for example, processor cache. The memory 820 may be any suitable computer-readable medium that stores computer-readable instructions for execution by computer-executable components. For example, the computer-readable instructions may be stored on one or a combination of RAM, ROM, flash memory, EEPROM, hard disk drive, solid state drive, or any other suitable device. In various embodiments, the computer-readable instructions include software stored in a non-transitory format. The processor 810, in conjunction with the software stored in the memory 820, executes an operating system and stored software applications. Various methods described elsewhere herein may be programmed as software instructions stored in the memory 820.

The interface 830 of some embodiments is a wireless network interface, which includes a receiver, a transmitter, or a receiver and transmitter for bi-directional communication. The receiver receives and demodulates data received over a communication network. The transmitter prepares data according to one or more network standards and transmits data over a communication network. In some embodiments, a transceiver antenna acts as both a receiver and a transmitter. Additionally or alternatively, in some embodiments, the interface 830 is a databus for sending and/or receiving data to one or more remote components via a wired connection. The interface 830 may additionally or alternatively include a user interface. The user interface may include a user input device, such as a button, a toggle, a switch, a touchscreen, or a keypad, and/or an output device such as a display screen, light display, audio output, or haptic output. The user input device may be configured to receive user commands to power the sensor on and off. In some embodiments, data about a user may also be input via the user input device.

In some embodiments, the control and processing module 800 is configured to process signals received from the optical fiber sensor to identify changes in propagated light intensity. In some such embodiments, the data on changes in propagated light intensity is transmitted to a remote computing device 850, via a wired or wireless connection, for a determination of applied forces and further processing. In some embodiments, the control and processing module 800 is configured to compute applied forces from changes in propagated light intensity. In some such embodiments, the data on applied forces is transmitted to a remote computing device 850 via a wired or wireless connection for further analysis. In other embodiments, the control and processing module 800 is configured to compute one or more of a user's posture and vital signs from the data on applied forces. In some such embodiments, the vital signs or posture data may be transmitted via a wired or wireless connection to an output device or a remote computing device 850 for storage or display.

Methods of Manufacture

Figure 9:
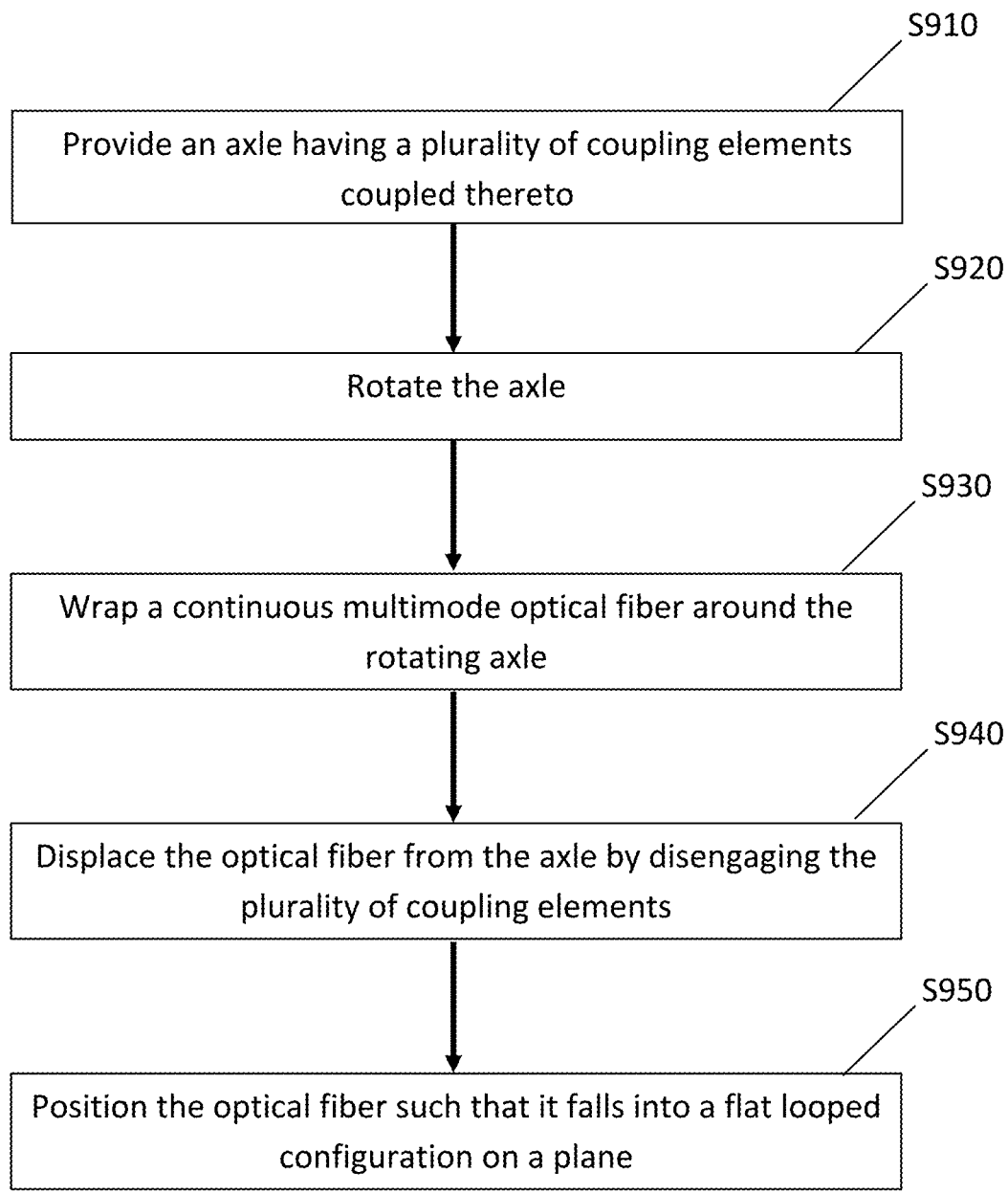
FIG. 9 illustrates a flow chart of one embodiment of a method for manufacturing a sensor for detecting micro-movements, in accordance with the present disclosure.

A means of manufacturing various embodiments of the optical fiber sensors described herein is provided in FIG. 9. As shown at S910, in some embodiments, an axle is provided. The axle is rotated at S920, and a multimode optical fiber is wrapped as a coil around the rotating axle at S930. The optical fiber is then displaced from the axle at S940, and positioned onto a plane where the wrapped coil falls into a flat looped arrangement at S950.

In some embodiments, the axle has a plurality of coupling elements coupled thereto, which rotate with rotation of the axle. In some such embodiments, the multi-mode optical fiber becomes engaged with the coupling elements on the axle while the continuous multi-mode optical fiber is wrapped around the rotating axle. In some embodiments, displacing the multi-mode optical fiber from the axle involves disengaging the plurality of coupling elements from the axle. In other embodiments, displacing the multi-mode optical fiber from the axle involves disengaging the multi-mode optical fiber from the coupling elements. In some embodiments, the plurality of coupling elements are equally or substantially equally spaced laterally on the axle. In some embodiments, the plurality of coupling elements include one or more of tape, glue, resin, other adhesive compound, hooks, latches, or other physical coupling elements.

Figure 10:
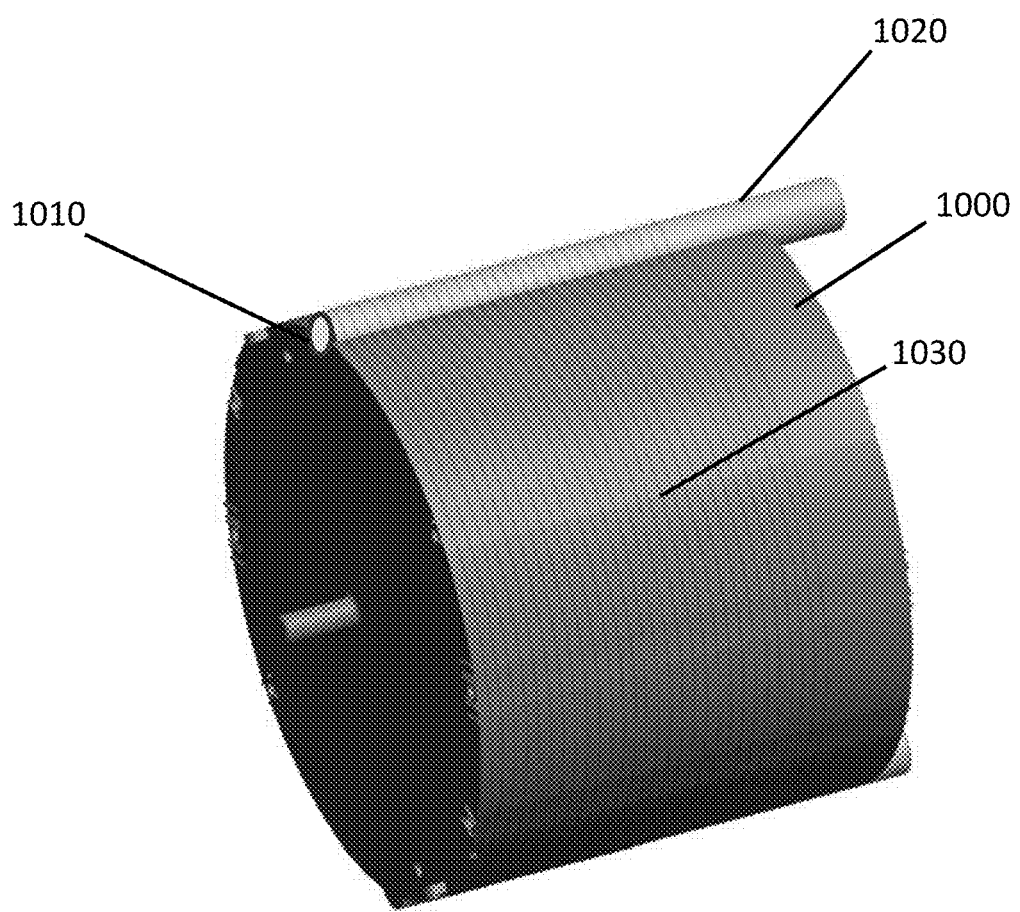
FIG. 10 illustrates a schematic diagram of one embodiment of an axle and wound optical fiber in the process of manufacturing a sensor for detecting micro-movements, in accordance with the present disclosure.

In still other embodiments, as shown in FIG. 10, the axle 1000 includes one or more grooves or other surface features 1010 running along a length of the axle surface in an axial direction. In such embodiments, a wedge, rod, or other tool 1020 can be inserted into the groove 1010. In some embodiments, the tool 1020 is wedged under the coiled multi-mode optical fiber 1030 and used to push the coiled fiber from the axle 1000 in a manner that will allow the coiled fiber 1030 to fall into a flat looped structure on a flat surface. In other embodiments, one or more rods or other tools 1020 are positioned in the grooves 1010 prior to the fiber 1030 being wound. In such embodiments, the tool 1020 may be slid out of the groove 1010 after the fiber 1030 is fully wound around the axle 1000. Doing so creates a space or slack that enables easy removal of the fiber 1030 from the coil 1000.

In some embodiments, the multi-mode optical fiber is wrapped around the axle by moving a mechanical arm axially, with respect to the axle, from a first position to a second as the axle rotates. The arm of such embodiments is configured to dispense the multi-mode optical fiber on the axle and is further configured to move axially one unit forward with each full rotation of the axle. In some embodiments, the unit size can be set to match a desired offset between each loop.

The size and shape of the axle determines the size and shape of the resultant loop. In some embodiments, the axle is interchangeable in order to create looped structures of different sizes and shapes.

Methods of Use

The optical fiber sensors described herein may be used in various applications requiring high fiber density/detection coverage and high sensitivity. For example, the described optical fiber sensors may be used to sense a person's ballistocardiogram waveform, heartbeat, breathing, subtle shifts in body weight indicative of posture, and/or other physiological parameters. In various embodiments, the physiological parameters are determined by detecting changes in fiber deformation caused by micro-movements of the human body.

Figure 11:
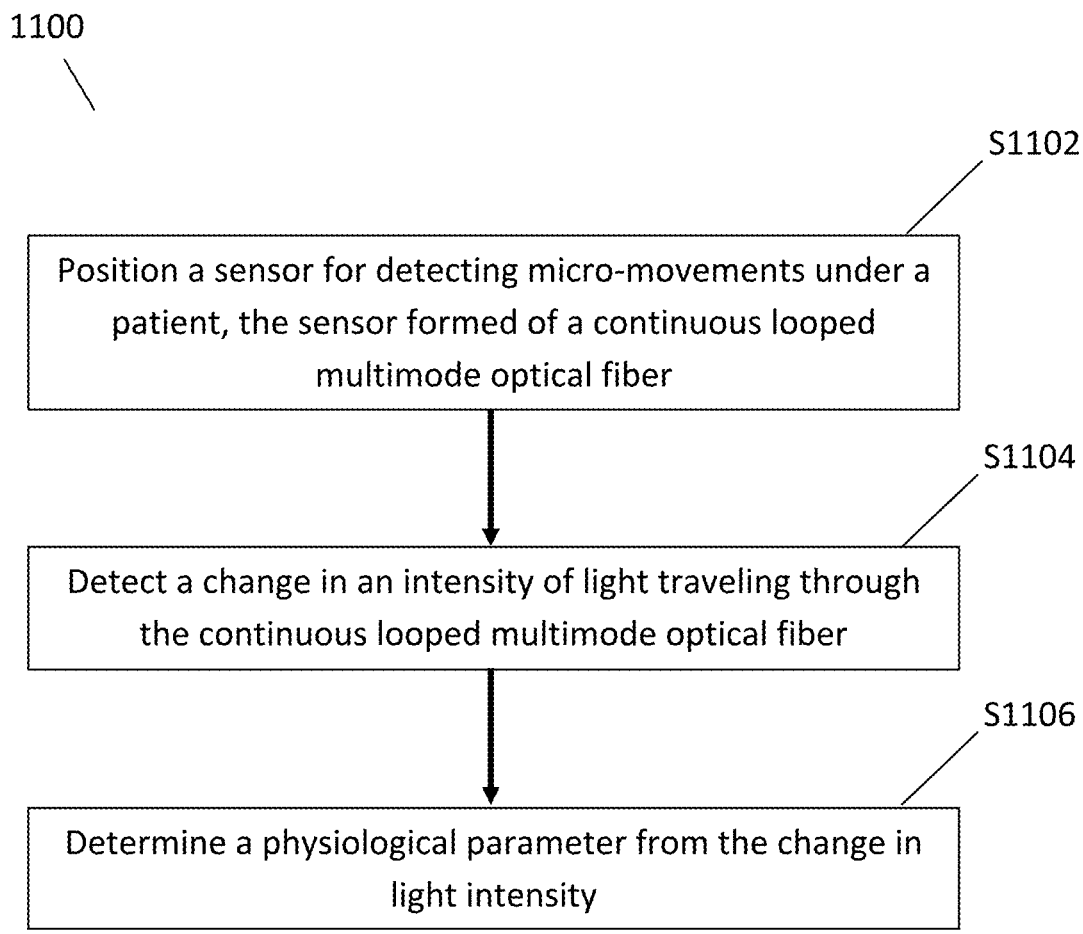
FIG. 11 illustrates a flow chart of one embodiment of a method for detecting patient health and activity information using an optical fiber sensor, in accordance with the present disclosure.

One embodiment of a method 1100 for detecting micro-movements and associated physiological parameters using an optical fiber sensor is provided in FIG. 11. As shown at S1102, in various embodiments, an optical fiber sensor is positioned under an individual. The optical fiber sensor may be embedded within, or form, a cushion. In some embodiments, the cushion is a portable seat cushion configured for placement on chairs (e.g., in an office, at home, etc.), bleachers, car seats, airplane seats, and/or other existing seat structures. In other embodiments, the cushion is integrated into an office chair, armchair, sofa, car seat, airplane seat, sleeping pod, mattress, or other structure. In some embodiments, the system includes multiple cushions, for example, two or more of: a backrest, an armrest, a seat, and a leg rest (e.g., ottoman, recliner, etc.). In other embodiments, the sensors are integrated into, or form, other structures such as, for example, a carpet or rug. Any one of these or other embodiments may be placed under the individual.

As described above, in various embodiments, the optical fiber sensor includes a fiber, a light source coupled to a first end of the fiber, a receiver coupled to a second end of the fiber, and one or more control and processing components. The fiber is arranged into a plurality of equally-sized loops disposed substantially in a plane, forming a looped structure, and each loop within the looped structure is partially overlapping, yet laterally offset from, neighboring loops. In various embodiments of the method, at S1104, light signals are received at the signal receiver and one or both of the receiver and a processing module detect a change in an intensity of light traveling through the looped structure. The detected change in light intensity may be temporal or spatial. That is, in some embodiments, the detected change in light intensity may be a change in intensity over time. The system may be configured to identify when the receiver receives more or less intense light. In other embodiments, the processing module is communicatively coupled to the light source and the signal receiver, and the detected change in light intensity is a change between the intensity of light originating at the light source and the intensity of light received at the signal receiver. In various embodiments, the change in light intensity corresponds to fiber deformation caused by one or more micro-movements of the human body. Upon detecting a change in light intensity, the processing module of various embodiments may, at S1106, determine one or more vital signs or other physiological parameters of a patient, as described in more detail, for example, in U.S. application Ser. No. 14/738,918 to Hu, which is incorporated by reference in its entirety. In sensors comprised of more than one looped structure, the detected physiological parameters of the patient may include weight or pressure distribution. For example, a processing module connected to a plurality of looped structures can detect how fiber deformation, and corresponding applied pressure, varies between the various looped structures.

In some embodiments, an average, minimum, maximum, healthy, and/or unhealthy vital sign, posture, or other physiological parameter is determined by the system when monitoring an individual over time. For example, the system may calibrate to the individual by monitoring the individual for a time period (e.g., hour, day, week, etc.) to determine the normal variability in the individual's cardiac and respiration waveforms and posture; the system may then detect deviations from the normal variability. Alternatively or additionally, the system may compare an individual's posture and cardiac and respiration waveforms to other individuals in the same age group, sex group, ethnic group, social class, work environment, location, and/or any other comparable group to identify deviations from normal or healthy values. Additionally or alternatively, the sensors may be used to track vital signs and/or posture in real-time or with a minimal delay.

As used in the description and claims, the singular form "a", "an" and "the" include both singular and plural references unless the context clearly dictates otherwise. For example, the term "a sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A sensor for detecting micro-movements, the sensor comprising:
    one looped structure or a plurality of looped structures, where each looped structure formed of a continuous multi-mode optical fiber arranged into a plurality of parallel equally-sized loops disposed substantially in a plane, wherein each loop within the looped structure is partially overlapping yet laterally offset from neighboring loops; where the laterally offset distance between each parallel neighboring loop and arranging the looped structure fiber segment in the looped structure is between 1 mm and 10 mm whereby the looped structure causes the optical fiber to cover significantly more of a surface;
    a light source coupled to a first end of the looped structure and configured to send light into the loop structure; and
    a receiver coupled to a second end of the looped structure, the receiver configured to sense changes in an intensity of light traveling through the looped structure.

2. The sensor of claim 1, wherein the continuous multi-mode optical fiber comprises a core diameter that is greater than 49% of a total diameter of the continuous multi-mode optical fiber.

3. The sensor of claim 1, wherein each of the loops are in a form shaped like a square, other rectangle, or other parallelogram, wherein the formed shape has rounded corners.

4. The sensor of claim 1, wherein each of the loops forms a circle or other ellipse.

5. The sensor of claim 1, wherein each of the loops forms a matching irregular shape.

6. The sensor of claim 1, wherein the continuous multi-mode optical fiber is formed of glass, plastic, or other suitable material.

7. The sensor of claim 1, wherein the distance between each parallel fiber segment is between 2 mm and 5 mm.

8. The sensor of claim 7, wherein the plurality of looped structures is formed of a single continuous multi-mode optical fiber such that each of the looped structures is directly connected to the other looped structures in the sensor.

9. The sensor of claim 7, wherein the plurality of looped structures comprises a plurality of multi-mode optical fibers, each of the multi-mode optical fibers forming a separate looped structure.

10. The sensor of claim 7, wherein the plurality of looped structures are positioned adjacent to each other on a plane.

11. The sensor of claim 7, wherein the plurality of looped structures partially or fully overlay each other.

12. The sensor of claim 1, further comprising a mesh structure, wherein the mesh structure is a single layer of mesh disposed above or below the optical fiber looped structure; or the mesh structure is formed of two layers of mesh which sandwich the optical fiber looped structure therebetween.

13. A method of manufacturing a looped structure, the of claim 1, the method comprising:
    providing an axle having a plurality of coupling elements coupled thereto;
    rotating the axle and the coupling elements;
    wrapping a continuous multi-mode optical fiber as a coil around the rotating axle, wherein the multi-mode optical fiber becomes engaged with the coupling elements on the axle; and
    displacing the multi-mode optical fiber from the axle by disengaging the plurality of coupling elements from the axle; using a wedge, rod, or other tool to push the coiled multi-mode optical fiber from the axle in a manner that will allow the coiled fiber to fall into a flat looped structure on a flat surface; wherein the looped structure is formed of the continuous multi-mode optical fiber neighboring loop and arranging the looped structure into a plurality of equally-sized loops disposed substantially in a plane, each loop within the looped structure is partially overlapping yet laterally offset from neighboring loops by a distance between 1 mm and 10 mm.

14. The method of claim 13, wherein the multi-mode optical fiber is wrapped around the rotating axle by moving an arm axially with respect to the axle from a first position to a second position parallel to the axle, the arm being configured to dispense the multi-mode optical fiber on the axle.

15. The method of claim 13, wherein the plurality of coupling elements are equally or substantially equally spaced laterally on the axle; the plurality of coupling elements comprise one or more of tape, glue, resin, other adhesive compound, hooks, latches, or other physical coupling elements.

16. The method of claim 13, wherein the axle includes one or more grooves running along a length of the axle surface in an axial direction; the tool inserted into the groove is wedged under the coiled multi-mode optical fiber and used to push the coiled fiber from the axle.

17. A method of detecting a physiological parameter, the method comprising:
    positioning a sensor for detecting micro-movements under a patient, the sensor for detecting micro-movements comprising:
        one looped structure or a plurality of looped structures, where each looped structure formed of a continuous multi-mode optical fiber arranged into a plurality of parallel equally-sized loops disposed substantially in a plane, wherein each loop within the looped structure is partially overlapping, yet laterally offset from, neighboring loops; where the laterally offset distance between each parallel neighboring loop fiber segment in the looped structure is between 1 mm and 10 mm the looped configuration causes the optical fiber to cover significantly more of a surface;
        a light source coupled to a first end of the looped structure and configured to send light into the loop structure; and
        a receiver coupled to a second end of the looped structure;
    detecting, by the receiver, a change in an intensity of light traveling through the looped structure, wherein the change in light intensity corresponds to fiber deformation caused by one or more micro-movements of the human body; and
    determining a physiological parameter from the change in light intensity.

18. The method of claim 17, wherein the physiological parameter comprises one or more of: a ballistocardiogram waveform, a heartbeat, breathing, body weight, body weight distribution on a surface or a shift in body weight or posture change.

\* \* \* \* \*